United States Patent [19]

Chao et al.

[11] Patent Number: 5,688,837
[45] Date of Patent: Nov. 18, 1997

[54] METHOD OF IMPROVING ADHESION OF POLYURETHANE FOAM TO POLYCARBONATE AND ARTICLES MADE THEREBY

[75] Inventors: Herbert Shin-I Chao, Schenectady; Carol Lynn Fasoldt, Averill Park, both of N.Y.; Abbas Mohamad Safieddine, Dearborn, Mich.; Christian Lietzau, Rhinebeck, N.Y.

[73] Assignee: General Electric Company, Schenectady, N.Y.

[21] Appl. No.: 533,051

[22] Filed: Sep. 25, 1995

Related U.S. Application Data

[60] Provisional application No. 60/001,892 Aug. 4, 1995.

[51] Int. Cl.⁶ ................................. C08G 18/00
[52] U.S. Cl. ............ 521/155; 428/412; 428/423.1; 428/423.3; 521/88; 521/89; 521/94; 521/97; 521/163; 521/174; 521/189

[58] Field of Search ................ 521/155, 163, 521/174, 189, 88, 89, 94, 97; 428/412, 423.1, 423.3

[56] References Cited

U.S. PATENT DOCUMENTS 4,769,030 9/1988 Pinchuk .......................... 427/2

*Primary Examiner*—John M. Cooney, Jr.
*Attorney, Agent, or Firm*—William H. Pittman

[57] ABSTRACT

A method improves the adhesion of polyurethane foam to polycarbonate by providing reactive groups on the polycarbonate surface. The adhesion is further improved by utilizing a polyurethane mix with an isocyanate index greater than 82. Articles comprising polycarbonate and polyurethane foam adhered to the polycarbonate by the method of the instant invention, such as automobile dashboards, are also provided.

20 Claims, No Drawings

METHOD OF IMPROVING ADHESION OF POLYURETHANE FOAM TO POLYCARBONATE AND ARTICLES MADE THEREBY

This application claims priority from provisional application Ser. No. 60/001892, filed on Aug. 4, 1995, the disclosure of which is hereby incorporated by reference.

BACKGROUND

This invention relates to a method for improving the adhesion of polyurethane foam to a polycarbonate surface.

Dashboards typically include a thermoplastic skeleton with a foam, such as polyurethane foam, applied to the skeleton. The polyurethane foam is typically produced by combining polyol and diisocyanate. Catalysts, surfactants and blowing agents can also be incorporated into the polyurethane mix.

The desired physical and mechanical properties of the resulting foam are obtained in part by adjusting the isocyanate index. The isocyanate index is calculated by multiplying 100 by the ratio of free isocyanate groups to isocyanate reactive groups, i.e., hydroxyl, amine and water, before reaction occurs. Therefore, an isocyanate index of 100 indicates that there are the same number of equivalents of isocyanate as there are the number of equivalents of hydroxyl, amine and water. Water has two equivalents per mole, a primary amine has two and a secondary amine has one. In the automotive industry, it is typical to produce a polyurethane mixture of polyol and diisocyanate with an isocyanate index of approximately 92.

This polyurethane foam is then covered with a skin, typically polyvinyl chloride. The preferred method of attaching the foam to the skeleton is to apply the foam reagents directly to the skeleton and then to allow them to foam onto the skeleton. In this way, the foam is attached to the skeleton without the use of primers or adhesives.

The automotive industry is moving toward an instrument panel design with a seamless, one-piece dashboard. In this type of design, the whole top side of the dashboard flips upwards when the airbags inflate from underneath the panel. This design requires that the skeleton be ductile to allow this sudden upward movement without shattering.

Currently, glass filled thermoplastics, such as poly(styrene-co-maleic anhydride) and poly(phenylene oxide), are used to manufacture the dashboard skeletons. These materials are often brittle at temperatures as low as −30° C. and may not meet the ductility requirements demanded by the active dashboard design. The new design requires an unfilled thermoplastic that is ductile at temperatures as low as −30° C. and high strain rates, and capable of adhering to the polyurethane foam without the use of additional surface coatings.

Impact modified polycarbonate has been shown to possess the necessary ductility. However, using the methods of the prior art, the polyurethane foam adheres to the polycarbonate skeleton only after the skeleton is first coated with a primer. This additional step adds material and labor costs. The instant invention provides a method which allows the adhering of the polyurethane foam directly on the polycarbonate skeleton without the use of the primer. It eliminates the additional steps and their associated costs.

The method of the instant invention is not limited to use in the production of dashboards, nor to use only in the automotive industry. It can be used in any application where it is desired to foam polyurethane directly on a polycarbonate surface, without the use of primers or other specialized coatings.

SUMMARY OF THE INVENTION

The instant invention provides a method for adhering polyurethane foam to polycarbonate comprising:

a. providing nucleophilic reactive radicals on a polycarbonate surface, b. generating a polyurethane mix comprising at least one polyol and at least one diisocyanate, wherein said polyurethane mix exhibits an isocyanate index of greater than 82, and, c. foaming the polyurethane mix on said polycarbonate surface.

The instant invention further provides articles which comprise polycarbonate foamed with a polyurethane mix according to the method of the instant invention.

DETAILED DESCRIPTION OF THE PREFERRED EMBODIMENTS

The instant invention provides a method whereby a polyurethane mix can be applied directly on a polycarbonate surface where it foams and adheres without additional surface coatings. Another aspect of the instant invention provides articles comprising polycarbonate foamed with polyurethane foam.

The manufacture of polycarbonate is well known in the art. There is no limit on the polycarbonate that can be employed in the instant invention. Appropriate polycarbonates for use in the instant invention include those materials that comprise structural units of the formula

wherein $R^1$ is a divalent organic radical. Suitable $R^1$ values include ethylene, propylene, trimethylene, tetramethylene, hexamethylene, dodecamethylene, 1,4-(2-butenylene), 1,10-(2-ethyldecylene), 1,3-cyclopentylene, 1,3-cyclohexylene, 1,4-cyclohexylene, m-phenylene, p-phenylene, 4,4'-biphenylene, 2,2-bis(4-phenylene)propane, benzene-1,4-dimethylene and similar radicals such as those which correspond to the dihydroxy compounds disclosed by name or formula (generic or specific) in U.S. Pat. No. 4,217,438, the disclosure of which is incorporated by reference herein. Also included are radicals containing non-hydrocarbon moieties. These may be substituents such as chloro, nitro, alkoxy and the like, and linking radicals such as thio, sulfoxy, sulfone, ester, amide, ether and carbonyl. Most often, however, all $R^1$ radicals are hydrocarbon radicals.

Preferably $R^1$ is aromatic. More preferably, the aromatic $R^1$ radicals have the formula

wherein each of $A^1$ and $A^2$ is a monocyclic divalent aromatic radical and Y is a bridging radical in which one or two atoms separate $A^1$ from $A^2$. The free valence bonds in formula II are usually in the meta or para positions of $A^1$ and $A^2$ in relation to Y.

In formula II, the $A^1$ and $A^2$ values may be unsubstituted phenylene or substituted derivatives thereof, illustrative substituents (one or more) being alkyl, alkenyl, halo (especially chloro and/or bromo), nitro, alkoxy and the like. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gem-alkylene (alkylidene) radical. Also included, however, are unsaturated radicals and radicals that contain atoms other than carbon and hydrogen; for example, 2,2-dichloroethylidene, carbonyl, phthalidylidene, oxy, thio, sulfoxy and sulfone. For reasons of availability and particular suitability for the purposes of this invention, the preferred radical of formula II is the 2,2-bis(4-phenylene)propane radical, which is derived from bisphenol A and in which Y is isopropylidene and $A^1$ and $A^2$ are each p-phenylene.

For use in the instant invention, the polycarbonate must have at least one type of nucleophilic reactive radical on its surface. Any nucleophile capable of reacting with the diisocyanate of the polyurethane mix can be provided on the polycarbonate surface as a nucleophilic reactive radical. Suitable nucleophilic reactive radicals include, but are not limited to, amino, hydroxyl, amide, and thiol groups. Preferably, the nucleophilic reactive radical is a hydroxyl group.

The nucleophilic reactive radicals can be provided by processing as the polycarbonate is manufactured. Nucleophilic reactive radicals can be formed on the polycarbonate during polymerization. For example, bisphenol A polycarbonate that has been produced by a melt transesterification process contains hydroxyl nucleophilic reactive radicals.

A polycarbonate that has nucleophilic reactive radicals can be blended with an inertly capped polycarbonate, which does not include any nucleophilic reactive radicals. It is not necessary that all of the polycarbonate in a blend possess nucleophilic reactive radicals.

It is also possible to obtain nucleophilic reactive radicals by treating the polycarbonate after it is polymerized. For example, surface hydroxyl radicals can be formed on inertly capped polycarbonate by hydrolysis. The polycarbonate surface can be treated with an alkaline reagent, such as KOH, to generate nucleophilic reactive radicals.

After polymerization, polycarbonate can also be subjected to processes such as reactive extrusion. During reactive extrusion, nucleophilic materials with nucleophilic reactive radicals, such as hydroxy groups, can be added to polycarbonate as it is extruded. During extrusion, the nucleophilic materials react with the polycarbonate, generating surface nucleophilic reactive radicals on the extruded polycarbonate.

Polycarbonate that has undergone a redistribution process after polymerization, such as that described in U.S. Pat. No. 5,414,057, can be provided with nucleophilic reactive radicals. Redistribution is a process whereby a polycarbonate having an initial weight average molecular weight is reformed into a redistributed polycarbonate composition having a weight average molecular weight which is different from the initial molecular weight. This can be accomplished by melt equilibrating a polycarbonate in the presence of a carbonate redistribution catalyst.

Polyurethane foam is generally produced by methods well known in the art. Typically, a polyurethane mix is generated by combining at least one polyol, typically a poly(oxyalkylene) polyol, and at least one diisocyanate, such as toluene diisocyanate or 4,4'-diphenylmethane diisocyanate, commonly known as methylene diphenyl diisocyanate, in proportions effective to generate the desired product. Also, catalysts, surfactants and blowing agents are typically present in the polyurethane mix.

For use in the present invention, the polyol and diisocyanate must be mixed in a proportion such that the isocyanate index is greater than 82. More preferably, the isocyanate index is 90 to 110.

The polyurethane mix can be applied to a surface of the polycarbonate by any means well known in the art, such as pouring and spraying. The polyurethane mix then reacts to produce polyurethane foam. As the mix foams, it adheres itself to the polycarbonate. The necessary reaction conditions, such as time and temperature, are well known to those skilled in the art. A skin can then be applied to the foam surface so that the foam surface is entirely covered. This skin can comprise materials such as polyvinyl chloride. This skin can be attached to the foam by methods well known in the art.

EXAMPLE

Adhesion of polyurethane foam to two grades of bisphenol A polycarbonate (polycarbonate) was evaluated. One grade is a low molecular weight (low MW) grade; the other is a high molecular weight (high MW) grade. The results are described in the following table. In each case, the polyurethane mix, from Textron Automotive Interiors of Farmington, N.H., which comprised UF1010B polyol and P100 diisocyanate, was poured onto the polycarbonate and allowed to foam. The resulting polyurethane foam had a density of approximately 6 lb/ft$^3$. The foam was then peeled from the polycarbonate surface. The polycarbonate/foam adhesion was rated qualitatively from "5", which indicates good adhesion, to "0", which indicates that no adhesion existed between the polycarbonate and foam.

The results clearly indicated that the adhesion depended on the concentration of nucleophilic reactive radicals on the polycarbonate surface and on the ratio of reagents in the foam mix. Under the standard foaming condition (isocyanate index of 92), the inertly capped polycarbonate (Lexan® 121 polycarbonate and Lexan 101 polycarbonate, products of General Electric Plastics, Pittsfield, Mass.) showed little adhesion to the foam. Only the hydroxyl nucleophilic reactive radical—enriched Lexan LX X28 polycarbonate had sufficient adhesion to the foam to qualify as a "pass". The Lexan LX X32 polycarbonate, which had fewer hydroxyl end groups than the LX X28 polycarbonate, showed marginal adhesion to the foam. Thus, under the standard foaming condition (isocyanate index of 92), only polycarbonate with nucleophilic reactive radicals showed any adhesion to the polyurethane foam.

However, once the isocyanate index was increased, the polycarbonate/foam adhesion improved drastically. While all four materials showed improved adhesion, particularly at an isocyanate index of 120, the LX materials with their nucleophilic reactive radicals demonstrated better adhesion than the inertly capped materials at the higher isocyanate index of 105.

Polycarbonate with nucleophilic reactive radicals can provide better adhesion than inertly capped polycarbonate to polyurethane foams with isocyanate indices of 92 and 105, which are, respectively, the same as and slightly higher than the standard indices currently used by the automotive industry.

|  |  | Isocyanate Index | | | |
|---|---|---|---|---|---|
|  |  | 120 | 105 | 92 | 82 |
| Lexan 121 (control) | 0% OH, low MW | pass (5) | pass (4) | fail (1) | fail (0) |
| Lexan LX X32 | 16% OH, low MW | pass (5) | pass (5) | marginal (2) | fail (0) |
| Lexan 101 (control) | 0% OH, high MW | pass (5) | pass (4) | fail (1) | fail (0) |
| Lexan LX X28 | 23% OH, high MW | pass (5) | pass (5) | pass (4) | fail (0) |

What is claimed is:

1. A method for adhering polyurethane foam to polycarbonate comprising:
   a. providing nucleophilic reactive radicals on a polycarbonate surface,
   b. generating a polyurethane mix comprising at least one polyol and at least one diisocyanate, wherein said polyurethane mix exhibits an isocyanate index of greater than 82, and,
   c. foaming the polyurethane mix on said polycarbonate surface.

2. A method according to claim 1, wherein said nucleophilic reactive radicals are selected from the group consisting of amino, hydroxyl, amide, and thiol groups.

3. A method according to claim 1, wherein said nucleophilic reactive radical comprises a hydroxyl group.

4. A method according to claim 1, wherein said nucleophilic reactive radicals are provided by processing as the polycarbonate is manufactured.

5. A method according to claim 4, wherein said polycarbonate is produced by melt transesterification.

6. A method according to claim 1, further comprising the step of blending the polycarbonate that has been provided with nucleophilic reactive radicals with a second polycarbonate that has substantially no nucleophilic reactive radicals.

7. A method according to claim 1, wherein said nucleophilic reactive radicals are provided by treating said polycarbonate after it is produced.

8. A method according to claim 7, wherein said polycarbonate is subjected to hydrolysis.

9. A method according to claim 7, wherein said polycarbonate is subjected to reactive extrusion.

10. A method according to claim 1, wherein said polyurethane mix comprises at least one polyol and at least one diisocyanate.

11. A method according to claim 1, wherein said polyol comprises a poly(oxyalkylene) polyol.

12. A method according to claim 1, wherein said diisocyanate is selected from the group consisting of toluene diisocyanate and methylene diphenyl isocyanate.

13. A method according to claim 1, wherein said polycarbonate comprises bisphenol A polycarbonate.

14. A method according to claim 1, wherein said polyurethane mix exhibits an isocyanate index of 90–110.

15. A method according to claim 14, wherein said polyol comprises a poly(oxyalkylene) polyol.

16. A method according to claim 14, wherein said diisocyanate is selected from the group consisting of toluene diisocyanate and methylene diphenyl isocyanate.

17. An article which comprises polycarbonate and a foamed polyurethane mix according to the method of claim 1.

18. An article in accordance with claim 17, further comprising
   a. a polycarbonate skeleton,
   b. polyurethane foam adhered at its lower surface to at least one surface of said polycarbonate skeleton, and,
   c. a skin attached to the upper surface of said polyurethane foam.

19. An article which comprises polycarbonate and a foamed polyurethane mix according to the method of claim 14.

20. An article in accordance with claim 19, further comprising
   a. a polycarbonate skeleton,
   b. polyurethane foam adhered at its lower surface to at least one surface of said polycarbonate skeleton, and,
   c. a skin attached to the upper surface of said polyurethane foam.

* * * * *